United States Patent
Slater

(10) Patent No.: US 6,603,545 B2
(45) Date of Patent: Aug. 5, 2003

(54) OPTICAL MEASUREMENT PROBE WITH LEAK MINIMIZATION FEATURES SUITED TO PROCESS CONTROL APPLICATIONS

(75) Inventor: Joseph B. Slater, Dexter, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 0 days.

(21) Appl. No.: 09/871,045

(22) Filed: May 31, 2001

(65) Prior Publication Data

US 2001/0048525 A1 Dec. 6, 2001

Related U.S. Application Data

(60) Provisional application No. 60/208,245, filed on May 31, 2000.

(51) Int. Cl.[7] ................................................. G01J 3/44
(52) U.S. Cl. ...................... 356/301; 356/432; 250/461.2
(58) Field of Search ................................ 356/301, 432; 385/31, 115, 119; 250/461.2

(56) References Cited

U.S. PATENT DOCUMENTS

| | | | | |
|---|---|---|---|---|
| 4,573,761 A | * | 3/1986 | McLachlan et al. | 385/115 |
| 4,577,110 A | * | 3/1986 | MacBride et al. | 250/461.2 |
| 4,803,365 A | * | 2/1989 | Krause et al. | 250/461.2 |
| 4,834,497 A | | 5/1989 | Angel | |
| 4,988,163 A | | 1/1991 | Cohen et al. | |
| 5,061,026 A | | 10/1991 | Clarke et al. | 385/31 |
| 5,182,791 A | | 1/1993 | Pollack | 385/147 |
| 5,974,211 A | * | 10/1999 | Slater | 385/33 |
| 5,986,756 A | * | 11/1999 | Slater et al. | 356/301 |
| 6,238,089 B1 | * | 5/2001 | Vodzak et al. | 374/208 |

* cited by examiner

Primary Examiner—Mark A. Robinson
(74) Attorney, Agent, or Firm—Gifford, Krass, Groh, Sprinkle, Anderson & Anderson, PC

(57) ABSTRACT

Various optical probe configurations are particularly suited to the monitoring of a process flow through the wall of a containment vessel. A probe body extends through, and is sealed to, the wall of the containment vessel. The probe body has an inner wall terminating in a distal end with a window, enabling light from the process flow to pass therethrough and into the probe body. In one embodiment, one or more lenses are disposed within the probe body to focus the light into a focal point, and a restriction of the inner wall of the probe body is used to create a narrow aperture at the focal point. In an alternative embodiment, a plug transparent to the light of interest is sealed to the inner wall of the probe body. As a further alternative, the elements include a second window creating a cavity with the distal window, and a port into the cavity accessible from outside the window for sampling purposes. Although these embodiments are referred to as 'alternative,' they may be used in combination as well as separately. Indeed, all three embodiments may be used simultaneously for increased integrity. In addition, although the probe body is presumed to carry light in both directions for excitation and collection, invention is not limited in this regard or the way in which light is carried to, or from, the body itself. That is, a probe according to the invention may be used only for excitation or collection, and optical fibers may, or may not, be used between the body and a source or radiation and/or analysis means.

3 Claims, 1 Drawing Sheet

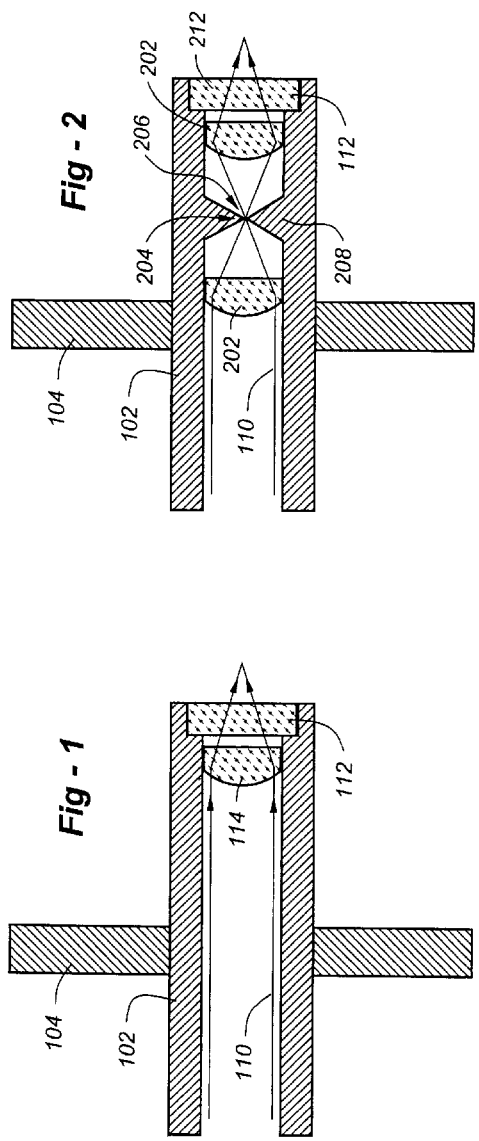
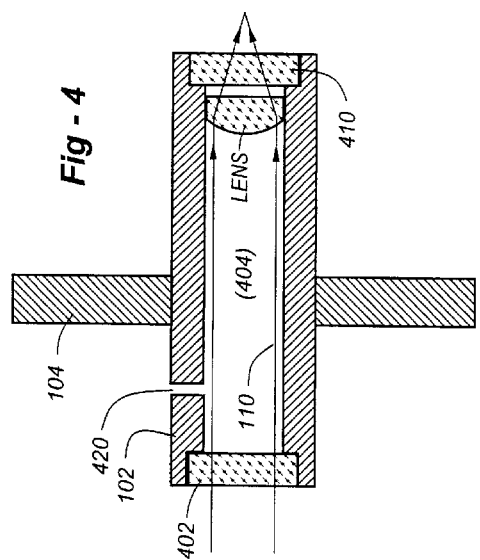
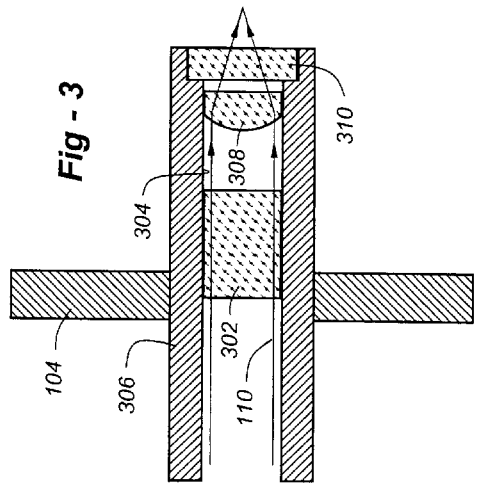
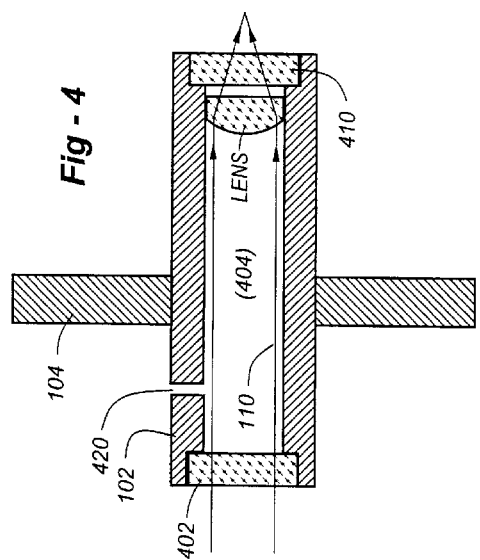

OPTICAL MEASUREMENT PROBE WITH LEAK MINIMIZATION FEATURES SUITED TO PROCESS CONTROL APPLICATIONS

REFERENCE TO RELATED APPLICATION

This application claims priority from U.S. provisional application Ser. No. 60/208,245, filed May 31, 2000, the entire contents of which are incorporated herein by reference.

FIELD OF THE INVENTION

This invention relates generally to optical measurement probes and, in particular, to a probe having leak-minimization features suited to on-line process control and other applications.

BACKGROUND OF THE INVENTION

Induced radiative effects such as Raman scattering and fluorescence have become extremely valuable tools associated with the non-destructive determination of molecular constituents. Optical probes for such purposes are being employed in on-line process control in increasing numbers. These probes are often installed directly into the process stream or reactor, thus posing a potential safety hazard.

Probes which are based on free-space optics are of particular concern. As seen in FIG. 1, the probe body 102 extends through the wall of process containment vessel 104. An optical beam 110 follows a direct path through a transparent medium such as window 112 to the sampling optics 114 immersed in the process. A failure of the window 112 at the immersed probe end allows a direct leak path to the outside.

The need remains, therefore, for an optical measurement probe with leak minimization and/or sampling suitable to process monitoring and other applications.

SUMMARY OF THE INVENTION

This invention resides in optical probe configurations particularly suited to the monitoring of a process flow through the wall of a containment vessel. All embodiments include a probe body which extends through, and is sealed to, the wall of the containment vessel. The probe body has an inner wall terminating in a distal end with a window, enabling light from the process flow to pass therethrough and into the probe body.

Although the probe body is presumed to carry light in both directions for excitation and collection, invention is not limited in this regard or the way in which light is carried to, or from, the body itself. That is, a probe according to the invention may be used only for excitation or collection, and optical fibers may, or may not, be used between the body and a source or radiation and/or analysis means.

In the preferred embodiment, the elements disposed within the probe body used to minimize and/or detect leaks of the process flow include one or more lenses operative to focus the light into a focal point, and a restriction of the inner wall of the probe body creating a narrow aperture at the focal point. In an alternative embodiment, a plug transparent to the light of interest is sealed to the inner wall of the probe body. As a further alternative, the elements include a second window creating a cavity with the distal window, and a port into the cavity accessible from outside the window for sampling purposes.

Although these embodiments are referred to as 'alternative,' they may be used in combination as well as separately. Indeed, all three embodiments may be used simultaneously for increased integrity.

BRIEF DESCRIPTION OF THE DRAWINGS

FIG. 1 is a cross sectional drawing of a probe based upon free-space optics to which the invention is applicable;

FIG. 2 depicts an embodiment of the invention wherein a pair of lenses is used to establish a focal point permitting the use of a narrow aperture through a restriction;

FIG. 3 shows an alternative embodiment of the invention wherein a transparent plug is sealed to the interior wall of a probe body; and FIG. 4 illustrates yet a further embodiment of the invention wherein a cavity is created for sampling purposes.

DETAILED DESCRIPTION OF THE INVENTION

A primary objection to the free-space design concept discussed above is the existence of a large-diameter opening to the outside if the window fails. FIG. 2 shows an embodiment of the invention, wherein lenses 202 are used to establish a focal point 204 permitting the use of a narrow aperture 206 through a restriction 208. By forming an optical relay, the effective leak aperture can be reduced to a very small size. In the case of modern Raman-type probes, this aperture can be on the order of several hundred microns.

FIG. 3 shows an alternative embodiment of the invention, wherein a plug 302 transparent to wavelengths of interest is sealed to the interior wall 304 of a probe body 306. By placing a solid plug of sapphire or other strong optically clear material (quartz, plastics, composites, etc.) behind the sampling lens 308, a failure of the window 310 does not compromise probe integrity.

FIG. 4 illustrates yet a further embodiment of the invention wherein a window 402 at the input (outside the process) side of the probe creates a cavity 404 for sampling purposes. In addition to providing a captive volume 404 between the two windows 402 and 410, a port 420 may be formed into which sensors (not shown) can be mounted to detect leaks or other problems.

I claim:

1. An optical measurement probe particularly suited to the monitoring of a process flow through the wall of a containment vessel, the probe comprising:

a probe body extending through and sealed to the wall of the containment vessel, the body having an inner wall and distal end with a window enabling light from the process flow to pass therethrough and into the probe body;

one or more elements disposed within the probe body for minimizing or detecting leaks of the process flow, including one or more lenses operative to focus the light into a focal point; and a restriction of the inner wall of the probe body creating a narrow aperture at the focal point.

2. The optical measurement probe of claim 1, wherein the elements further include:

a transparent plug sealed to the inner wall of the probe body.

3. An optical measurement probe particularly suited to the monitoring of a process flow through the wall of a containment vessel, the probe comprising:

a probe body extending through and sealed to the wall of the containment vessel, the body having an inner wall and distal end with a window enabling light from the process flow to pass therethrough and into the probe body;

one or more lenses operative to focus the light into a focal point; and a restriction of the inner wall of the probe body creating a narrow aperture at the focal point.

* * * * *